United States Patent
Kaltner et al.

(10) Patent No.: US 8,933,705 B2
(45) Date of Patent: Jan. 13, 2015

(54) SENSOR ELECTRONICS FOR A PLURALITY OF SENSOR ELEMENTS AND METHOD FOR DETERMINING A POSITION OF AN OBJECT AT THE SENSOR ELEMENTS

(75) Inventors: Claus Kaltner, Bergkirchen (DE);
Holger Steffens, München (DE)

(73) Assignee: Microchip Technology Germany GmbH II & Co. KG, Ismaning (DE)

(*) Notice: Subject to any disclaimer, the term of this patent is extended or adjusted under 35 U.S.C. 154(b) by 269 days.

(21) Appl. No.: 13/508,776

(22) PCT Filed: Nov. 11, 2010

(86) PCT No.: PCT/EP2010/067318
§ 371 (c)(1),
(2), (4) Date: Aug. 2, 2012

(87) PCT Pub. No.: WO2011/058116
PCT Pub. Date: May 19, 2011

(65) Prior Publication Data
US 2012/0286802 A1    Nov. 15, 2012

(30) Foreign Application Priority Data

Nov. 11, 2009    (DE) .................. 10 2009 052 537

(51) Int. Cl.
*G01R 27/04*    (2006.01)
*G01R 27/32*    (2006.01)
(Continued)

(52) U.S. Cl.
CPC ............ *G06F 3/044* (2013.01); *G01N 27/4148* (2013.01); *G01R 27/2605* (2013.01);
(Continued)

(58) Field of Classification Search
CPC ............... H03K 17/955; H03K 2217/960775; H03K 17/962; H03K 2217/96015; H03K 2217/960745; H03K 2217/960765; G01D 5/24; G01B 7/023; G01V 3/088; G01R 27/2605; G01R 29/14; G06F 3/044; G06F 3/03547; G01N 27/4148; G01N 33/48728; G11C 27/024

USPC .......... 324/76.11–76.83, 600, 629, 684, 686, 324/662–679, 658, 661, 519, 548, 750.17; 340/407.2, 815.4, 870.37, 562, 545.4; 345/156, 159, 173, 174; 704/246, 704/E17.003
See application file for complete search history.

(56) References Cited

U.S. PATENT DOCUMENTS 4,016,490 A *  4/1977  Weckenmann et al. ....... 324/671
6,744,258 B2 *  6/2004  Ishio et al. ..................... 324/548
(Continued)

FOREIGN PATENT DOCUMENTS

| GA | 2451267 A | 1/2009 | ............. G06F 3/044 |
| GB | 2072389 A | 9/1981 | ............. G06F 3/023 |

(Continued)

OTHER PUBLICATIONS

WO 2008/116642; Machine Translation.*
(Continued)

*Primary Examiner* — Vinh Nguyen
*Assistant Examiner* — Raul Rios Russo
(74) *Attorney, Agent, or Firm* — King & Spalding L.L.P.

(57) ABSTRACT

An electronic circuit with a plurality of connections for a plurality of sensor elements is provided, wherein the electronic circuit is configured to detect, with at least one multiplexing method, the presence of an object in at least one observation area of the sensor elements and to distinguish between the sensor elements. Also a method for determining the position of at least one object situated in at least one observation area of sensor elements relative to the sensor elements is provided, whereby with a multiplexing method an electric variable for each sensor element is detected, which is indicative for the presence of the object in the respective observation area.

20 Claims, 6 Drawing Sheets

(51) Int. Cl.
  *G06F 3/044* (2006.01)
  *G01N 27/414* (2006.01)
  *G01D 5/24* (2006.01)
  *G01R 31/12* (2006.01)
  *G01R 27/26* (2006.01)
  *G01V 3/08* (2006.01)

(52) U.S. Cl.
  CPC . *G01D 5/24* (2013.01); *G01V 3/088* (2013.01)
  USPC ............ 324/629; 324/548; 324/658; 324/684

(56) References Cited

U.S. PATENT DOCUMENTS

| | | | | |
|---|---|---|---|---|
| 6,859,141 | B1* | 2/2005 | Van Schyndel et al. | 340/562 |
| 7,084,641 | B2* | 8/2006 | Brederlow et al. | 324/658 |
| 2005/0068044 | A1 | 3/2005 | Peine et al. | 324/658 |
| 2006/0250142 | A1* | 11/2006 | Abe | 324/663 |
| 2007/0269012 | A1* | 11/2007 | Somers | 378/117 |
| 2008/0061800 | A1* | 3/2008 | Reynolds et al. | 324/678 |
| 2009/0160461 | A1* | 6/2009 | Zangl et al. | 324/684 |

FOREIGN PATENT DOCUMENTS

| | | | | |
|---|---|---|---|---|
| JP | 07084712 | A | 3/1995 | ................ G06F 3/03 |
| JP | 09292950 | A | 11/1997 | .............. G06F 3/033 |
| WO | 2008/116642 | A2 | 10/2008 | ................ G06F 3/01 |
| WO | 2009/130165 | A2 | 10/2009 | .............. G06F 3/033 |

OTHER PUBLICATIONS

International PCT Search Report, PCT/EP2010/067318, 3 pages, Mar. 15, 2011.
Japanese Office Action, Application No. 2012538338, 10 pages, Aug. 5, 2014.

* cited by examiner

SENSOR ELECTRONICS FOR A PLURALITY OF SENSOR ELEMENTS AND METHOD FOR DETERMINING A POSITION OF AN OBJECT AT THE SENSOR ELEMENTS

CROSS-REFERENCE TO RELATED APPLICATIONS

This application is a U.S. National Stage Application of International Application No. PCT/EP2010/067318 filed Nov. 11, 2010, which designates the United States of America, and claims priority to DE Patent Application No. 10 2009 052 537.8 filed Nov. 11, 2009. The contents of which are hereby incorporated by reference in their entirety.

TECHNICAL FIELD

The invention relates to a sensor electronics with connections for a plurality of sensor elements, especially capacitive sensor elements, as well as a method for determining the position of an object, for example a finger, relative to a plurality of sensor elements, which are coupled with the sensor electronics according to various embodiments.

BACKGROUND

From prior art sensor systems are known which have a number of sensors, which are coupled with the sensor electronics, for example an evaluating device. In this respect it is disadvantageous, that for each sensor an own sensor electronic unit or evaluating device has to be provided in order to run the single sensors or to test the sensor signals. If the sensor electronic unit or the evaluating devices are provided in the form of an integrated electronic circuit, the connection of every further sensor is made with a considerable expensive material and expenditure.

Further, additionally expensive material and expenditure result from additional connectors provided at the integrated component.

In capacitive sensor systems which provide a plurality of capacitive sensors, an additional disadvantage is that a certain distance between the capacitive sensors has to be maintained, in order to prevent alternating electric fields from coupling into adjacent capacitive sensors. In order to reduce the distance of two adjacent capacitive sensors, additional measures are necessary in order to shield two adjacent capacitive sensors from each other. Thus, on an integrated circuit sufficient additional connectors have to be provided, at which the corresponding shielding means can be connected.

SUMMARY

The object of the present invention was therefore to provide solutions which on the one hand allow the number of sensor elements on a sensor electronic unit to be increased, without at the same time having to considerably increase the hardware components of the sensor electronic unit, and on the other hand at the same time allow a plurality of capacitive sensor elements to be established and run, even with a small distance to each other, with at the same time an improved detection of the position of an object in the observation areas of the capacitive sensor elements.

This object is solved according to the invention by a sensor electronic unit with connections for a plurality of sensor elements as well as by a method for determining the position of an object situated in at least one observation area of the sensor elements according to the independent claims. Advantageous embodiments of the invention result from the respective independent claims.

Therefore, an electronic circuit with a plurality of connections for a plurality of sensor elements is provided, wherein the connections of the electronic circuit may be coupled with at least one transmission electrode, at least one reception electrode and at least one compensation electrode, which form a sensor element, whereby the at least one compensation electrode may be capacitively coupled with the at least one reception electrode and whereby at least one alternating electrical field at the sensor element forms an observation area of the sensor element, and whereby the electronic circuit is configured to detect, with at least one multiplexing method, the presence of at least one object in at least one observation area of the sensor elements and to distinguish the sensor elements from each other.

It is advantageous to arrange the at least one compensation electrode between the at least one transmission electrode and the at least one reception electrode of the sensor element.

The at least one electric alternating field at the sensor element may be formed by a first alternating electric field emitted at the transmission electrode and by a second alternating electric field emitted at the compensation electrode, whereby the first alternating electric field and the second alternating electric field may be coupled into the reception electrode.

The first alternating electric field emitted at the transmission electrode may be coupled into the reception electrode when an object enters the observation area of the sensor element. The second alternating electric field emitted at the compensation electrode may be coupled into the reception electrode even if there is no object in the observation area of the sensor element. An approach of an object to a sensor element may cause a coupling of the first alternating electric field emitted at the transmission electrode into the reception electrode, whereby the first alternating electric field is coupled by means of the object into the reception electrode. By coupling the first electric alternating field emitted at the transmission electrode into the reception electrode by means of the object, the first alternating electric field is practically withdrawn from the sphere of the second alternating electric field emitted at the compensation electrode. The second alternating electric field is then practically "bridged", i.e. the first alternating electric field is no longer deleted or less attenuated by the second alternating electric field.

By multiplexing a particularly advantageous multiple use of hardware components of the electronic circuit is possible, because parts of the signal paths in the electronic circuit need to be provided only once for several sensor elements.

The electronic circuit may be configured in such a way that in multiplexing a first alternating voltage is supplied to each transmission electrode of the sensor elements, a second alternating voltage to each compensation electrode of the sensor elements, and a current flowing through the respective reception electrode of the sensor elements is detected, whereby for each sensor element the first alternating voltage and the second alternating voltage have the same frequency and are dephased with each other.

The multiplexing method may be a frequency multiplexing method and the first alternating voltage supplied to the transmission electrodes of the sensor elements may have each a different frequency.

A connection of the electronic circuit may be coupled with the reception electrodes of the sensor elements by means of a common electric conductor, wherein the electronic circuit is configured in such a way that the total current which results from the current flowing in the respective reception electrodes is submitted to a frequency analysis, in order to determine a value for every reception electrode which is representative for the presence of the object at the respective sensor element.

The multiplexing method may be a time division method and the electronic circuit may be configured to supply the transmission electrodes of the sensor elements with the first alternating voltage one after the other.

The electronic circuit may be configured to add the current flowing through the respective reception electrodes of the sensor elements.

The electronic circuit may be further configured to fade out the currents of the reception electrodes at which the current is not detected.

The multiplexing method may be a time division method and the electronic circuit may be configured to detect sequentially the current flowing through the respective reception electrodes of the sensor elements and to determine a value from the detected current, which is representative for the presence of the object at the respective sensor element.

The electronic circuit may be configured to couple the transmission electrodes, which are not supplied with the first alternating voltage and/or the reception electrodes, at which the current is not detected, with the mass potential of the electronic circuit.

The multiplexing method may be a code division multiplexing method, whereby the electronic circuit is configured to code the first alternating voltage, which with the transmission electrodes of the sensor elements can be supplied, each time with a different code.

The electronic circuit may be configured to undergo a decoding of the total current which results from the current flowing through the respective reception electrodes, in order to determine a value for every reception electrode, which is representative for the presence of the object at the respective sensor element.

The electronic circuit may be configured to supply the compensation electrode of the sensor elements each time with at least one part of the first alternating voltage.

The compensation electrodes of the sensor elements may be formed by a common compensation electrode, in which a connection of the electronic circuit is provided for connecting the common compensation electrode.

Alternatively or additionally the reception electrodes of the sensor elements may be formed by a common reception electrode, in which a connection of the electronic circuit is provided for connecting the common reception electrode.

Alternatively or additionally the transmission electrodes of the sensor elements may be formed by a common transmission electrode, in which a connection of the electronic circuit is provided for connecting the common transmission electrode.

It has been found to be advantageous to form the sensor elements by a common transmission electrode, a number of reception electrodes and at least one compensation electrode. The at least one compensation electrode may be formed as a common compensation electrode or as a number of compensation electrodes.

Also a method is provided for determining the position of at least one object relative to the sensor elements situated in at least one observation area of the sensor elements, wherein an electric variable is detected with a multiplexing method for each sensor element, which is indicative for the presence of the object in the respective observation area.

A sensor element may comprise at least one transmission electrode (SE), at least one reception electrode (EE) and at least one compensation electrode (KE).

The at least one compensation electrode may be arranged between the at least one transmission electrode and the at least one reception electrode of the sensor element.

An alternating electrical field, which is formed by a first alternating electric field emitted at the transmission electrode and by a second alternating electric field emitted at the compensation electrode, constitutes the observation area of the sensor element.

The first alternating electric field and the second alternating electric field may be coupled into the reception electrode.

The first alternating electric field emitted at the transmission electrode may be coupled into the reception electrode when an object enters the observation area of the sensor element.

Between the detected electric variables an interpolation may be performed in order to determine an interpolated position of the at least one object relative to the sensor elements.

It is advantageous to assign an ordinal number to each sensor element, which describe an adjacent relationship between the sensor elements and wherein the interpolation comprises detection of a first sensor element, which shows the highest value of the detected electric variable, detection of a second sensor element from the directly adjacent sensor elements, which shows the highest value of the detected electric variable, and calculation of an interpolated position of the at least one object relative to the sensor elements from the ordinal numbers of the first and the second sensor element and from the values of the detected electric variables of the first and the second sensor element.

The interpolated position may be calculated according to the formula $$(n1 \cdot v1 + n2 \cdot v2)/(v1+v2),$$

wherein $n1$ is the ordinal number of the first sensor element, $n2$ is the ordinal number of the second sensor element, $v1$ is the value of the detected electric variable of the first sensor element and $v2$ is the value of the detected electric variable of the second sensor element.

BRIEF DESCRIPTION OF THE DRAWINGS

Further details and characteristics of the invention result from the following description in association with the drawing. The figures show.

DETAILED DESCRIPTION

Figure 1:
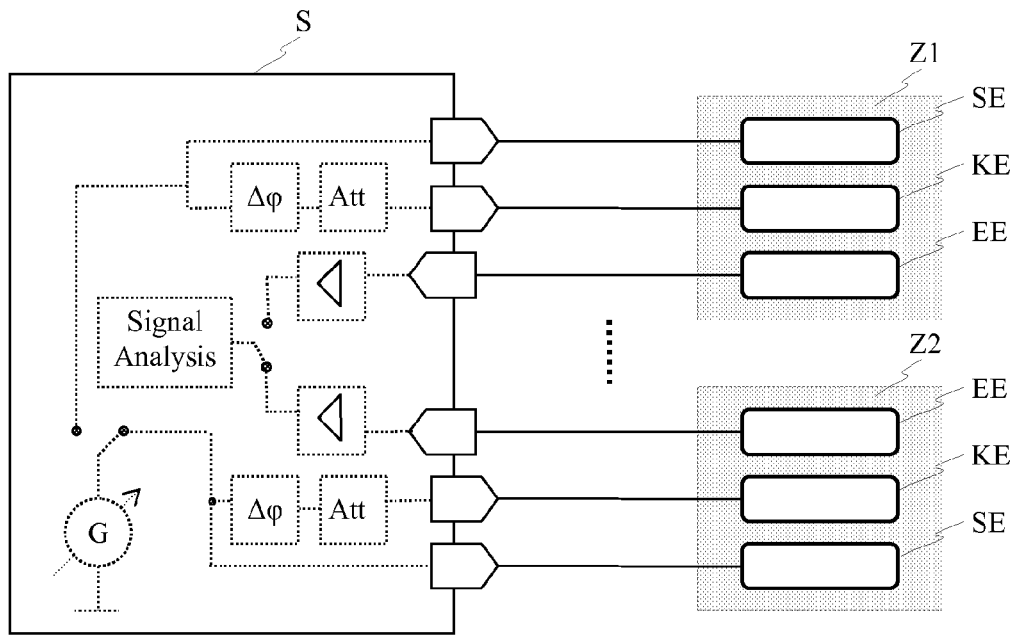
FIG. 1 a sensor electronic circuit with connections for a plurality of sensor elements, whereby for each sensor element a corresponding connection is provided.

FIG. 1 shows a capacitive sensor system with an electronic circuit S according to the invention, to which two sensor elements Z1 and Z2 are connected. The electronic circuit S will be designated in the following as sensor electronic unit S. Each of the two sensor elements comprises one transmission electrode SE, one compensation electrode KE and one reception electrode EE. The electrodes are coupled by means of a connection A of the sensor electronics with the sensor electronics. The transmission electrodes SE are each supplied with a first alternating voltage, so that from each transmission electrodes SE a first alternating electrical field is emitted. The two compensation electrodes KE are each supplied with a second alternating voltage, so that at each compensation electrode KE another alternating electrical field is emitted.

The second alternating voltage is preferably dephased with respect to the first alternating voltage. The first alternating voltage may be for example a sinus signal, whereas the second alternating voltage may be for example a rectangular signal. Both signals may also have a rectangular signal form. The first and/or the second alternating voltage may be different for each sensor element.

A part of the first electric alternating voltage may also be added to the second alternating voltage, so that the compensation electrodes KE are supplied with an electric alternating voltage which is the sum of a part of the first alternating voltage and a part of the second alternating voltage. For this purpose the corresponding signal paths in the sensor electronic unit S may be coupled with each other. The addition of only a part of the first alternating voltage to the second alternating voltage may be achieved by conducting the first alternating voltage initially to an attenuator. Alternatively the transmission electrode SE and the compensation electrode KE may also be coupled with each other by means of a attenuator.

The alternating electric field emitted at the transmission electrode SE or at the compensation electrode KE is coupled into the reception electrode EE, so that an electric current flows through the reception electrode EE. The electric current flowing through the reception electrode EE may be detected by an evaluating device, which is a component of the sensor electronic unit S.

The sensor elements Z1 and Z2 shown in FIG. 1 may be operated for example in the time-division multiplexing method, i.e. each time only one of the two sensor elements Z1, Z2 is active. Thus the sensor electronic unit S has only to provide one signal generator, the signal of which is applied at the transmission electrode SE or at the compensation electrode KE. Also only one evaluating device needs to be provided for the evaluation or detection of the current flowing in the reception electrode EE. Alternatively the sensor elements Z1, Z2 may be also operated with a frequency-based multiplexing, i.e. the transmission electrode and the compensation electrode of the first sensor item Z1 are supplied with a signal, the frequency of which is different from the signal which the transmission electrode SE and the compensation electrode KE of the second sensor item Z2 are supplied with.

Figure 2:
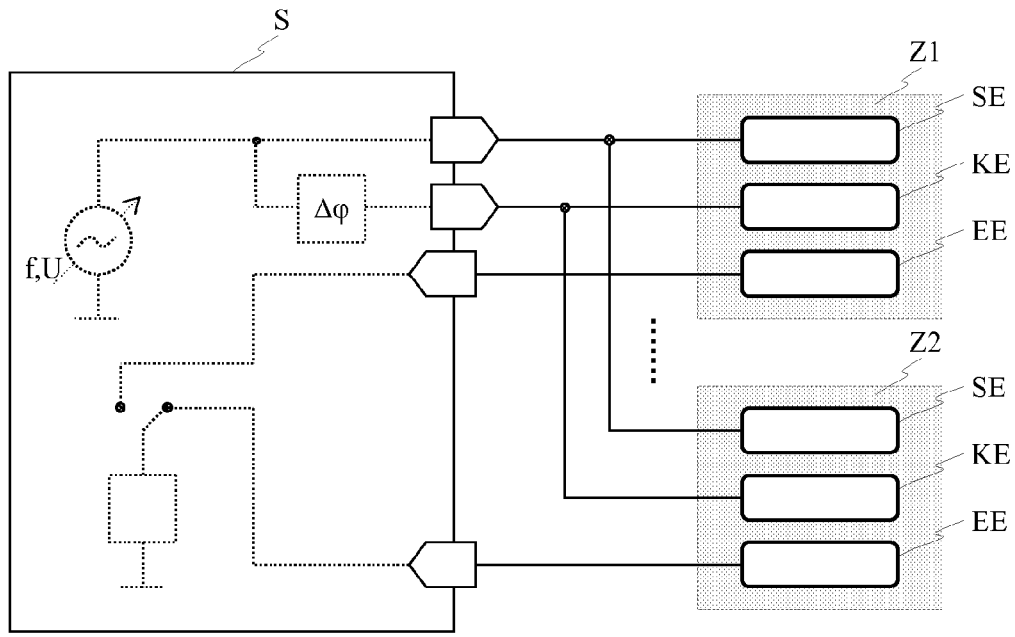
FIG. 2 an embodiment of a sensor electronics according to to 4 the invention which may be coupled with a plurality of sensor elements and whereby a number of connections of the sensor electronics are provided for the connection of several electrodes of different capacitive sensor elements.

FIG. 2 shows a capacitive sensor system with a sensor electronic unit according to the invention, to which two capacitive sensor elements Z1 and Z2 are connected. Each one of the two sensor elements Z1, Z2 includes one transmitter electrode SE, one compensation electrode KE and one reception electrode EE.

The sensor elements Z1, Z2 may each also include several transmission electrodes SE and/or several compensation electrodes KE and/or several reception electrodes EE as described in the embodiment according to FIG. 2 as well as in the embodiments described in the following figures. For example a sensor element may include a transmission electrode, a compensation electrode and several reception electrodes. A sensor element may also include several transmission electrodes, several compensation electrodes and a common reception electrode.

The sensor electronic unit S has a connection to which the transmission electrodes SE of the two sensor elements Z1, Z2 are connected by means of a common electric main. The sensor electronic unit S has a further connection to which the compensation electrodes KE of the two sensor elements Z1, Z2 are connected by means of a common electric main. The sensor electronic unit S further has two more connectors to which is connected each time one reception electrode EE of the two sensor elements Z1, Z2.

The transmission electrodes SE of the two sensor elements Z1, Z2 are each supplied with a first alternating voltage, so that from each transmission electrode SE an alternating electrical field is emitted. The two compensation electrodes KE are each supplied with a second alternating voltage $U_2$, so that at each compensation electrode KE another alternating electrical field is emitted. The second alternating voltage supplied to the compensation electrodes KE is preferably dephased with respect to the first alternating voltage, with which the transmission electrodes SE are supplied. The sensor electronic unit S for this purpose may provide a signal generator, which is coupled with the first connection, to which the transmission electrodes SE are connected, and which is coupled by a phase shifter over the second connection, to which the compensation electrodes KE are connected. Alternatively the phase shifter may also be provided between the signal generator and the first connection.

The sensor electronic unit S further includes an evaluation circuit, which by means of a multiplexer is coupled with the connections to which the reception electrodes EE are connected. Thus, the single reception electrodes EE could be queried sequentially, i.e. an electric variable of the reception electrodes EE may be detected sequentially. The electric variable of the reception electrodes may be a current which flows if the electric alternating field emitted at the transmission electrode SE and at the compensation electrode KE is coupled into the reception electrode EE. The first alternating voltage $U_1$ and the second alternating voltage $U_2$ are preferably selected in such a way that the alternating field emitted at the transmission electrode SE is only coupled into the reception electrode EE if an object enters the observation area of the sensor element. Alternatively a small coupling may be present in the normal state for system monitoring. A value may be given to the current detected at the respective reception electrode EE, which is representative for the presence of an object at the respective sensor element Z1, Z2.

By connecting, according to the invention, the transmission electrodes SE and the compensation electrode KE to each connection of the sensor electronic unit S and by detecting the electric variable at the respective reception electrode EE in the multiplexing, the number of connectors at the sensor electronic unit can be maintained low. The maximum number of connectors results from the number of sensor elements plus two connectors for the transmission electrodes or the compensation electrodes (i.e. number of connectors=number of sensor elements+2). As the reception electrodes EE are coupled sequentially with an evaluating device of the sensor electronic unit, every sensor element may be also unequivocally identified, even if all transmission electrodes SE or all compensation electrodes KE of the sensor elements Z1, Z2 are each supplied with the identical first alternating voltage $U_1$ or with the identical second alternating voltage $U_2$.

Figure 3:
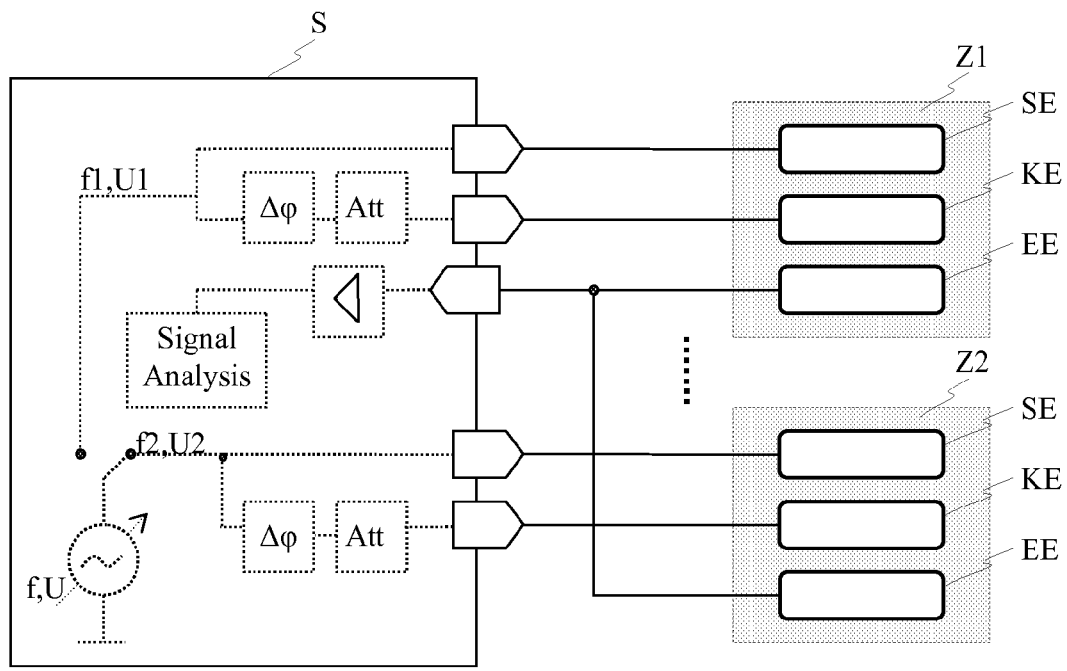

FIG. 3 shows another embodiment of a sensor electronic unit S according to the invention, to which two sensor elements Z1, Z2 are connected. According to the embodiment shown in FIG. 3, the sensor electronic unit S provides a connection for each transmission electrode SE. Also the sensor electronic unit S provides a connection for each compensation electrode KE. However, the reception electrodes EE of the sensor elements Z1, Z2 are connected by means of a common electric main to a particular connection of the sensor electronic unit S.

In a variant of the embodiment shown in FIG. 3, the transmission electrode SE of the first sensor element Z1 and the transmission electrode SE in the time-division multiplexing of the second sensor element Z2 may be supplied with a first electric alternating voltage $U_1$. Also the compensation electrode KE of the first sensor element Z1 and the compensation electrode KE in the time-division multiplexing of the second sensor element Z2 are supplied with a second alternating voltage, which is preferably dephased with respect to the first alternating voltage. The phase shift of the second alternating voltage $U_2$, with respect to the first alternating voltage U1 may be done here with the help of a phase shifter.

As the transmission electrode SE and the compensation electrode KE are each supplied sequentially with the corresponding alternating voltage, an evaluating device of the sensor electronic unit S, to which all reception electrodes EE of sensor elements Z1, Z2 are connected, can undertake a precise attribution of a detected sensor signal to the respective sensor element Z1, Z2.

In a second variant of the sensor electronic unit S according to FIG. 3, the transmission electrodes SE can be each supplied with a first alternating voltage of different frequency. The respective compensation electrode is here supplied with a second alternating voltage of equal frequency, which is dephased with respect to the first alternating voltage. A phase shift may be done again with a phase shifter. As the transmission electrodes SE and the compensation electrodes KE of the sensor elements are each supplied with an alternating voltage of different frequency, also an alternating electrical field of different frequency is formed at each of the transmission electrodes and of the compensation electrodes. The current generated by the alternating electric field coupled in the corresponding reception electrodes EE thus also has a different frequency. The frequency spectrum at the connection, to which the reception electrodes EE are connected, may be divided into the single frequency components in an evaluation unit of the sensor electronic unit S with the help of a frequency analysis, for example a Fast Fourier transformation or a Gortzel algorithm. The currents resulting from the frequency analysis can be again precisely assigned to a sensor element Z1, Z2.

In a third variant of the sensor electronic unit shown in FIG. 3 the alternating signal may be provided by a signal generator coded with a code, in which the code is different for each transmission electrode SE. The coded alternating signal is supplied to the transmission electrode. A alternating signal dephased with respect to the coded alternating signal is supplied to the corresponding compensation electrode. The signal at the entry of the sensor electronic unit S may be decoded again by means of the code. The currents resulting from the decoding may be again precisely assigned to the respective sensor element Z1, Z2.

In the embodiment according to FIG. 3, the maximum number of connections which are necessary to connect a plurality of sensor elements results from the number of sensor elements plus one connection (i.e. 2×number of sensor elements+1).

Figure 4:
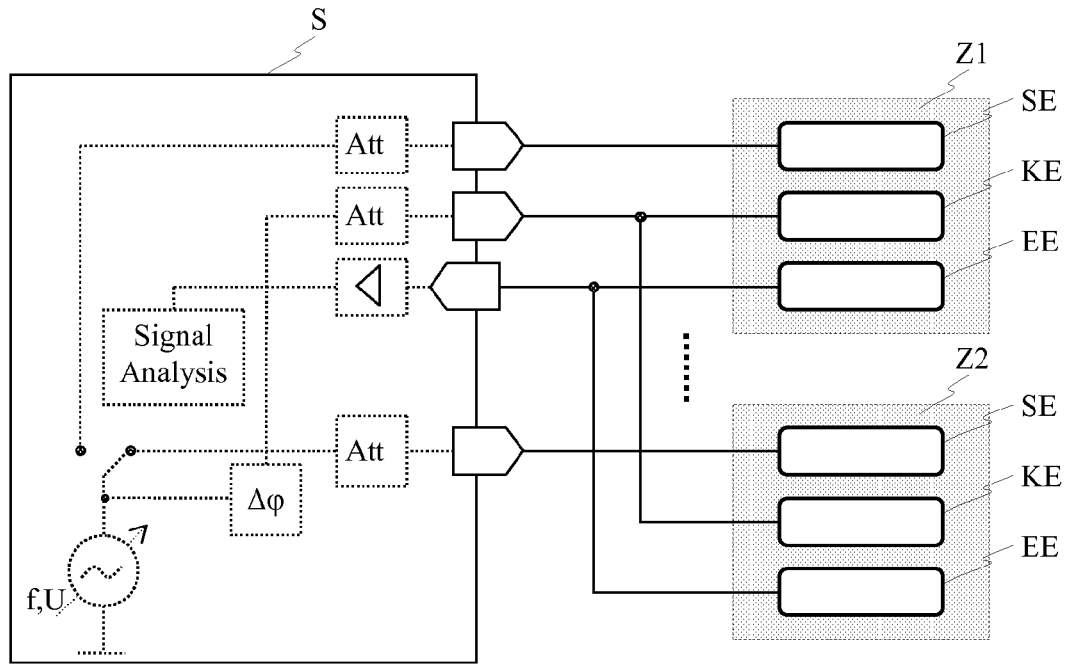

FIG. 4 shows an embodiment of a sensor electronic unit S according to the invention, to which two sensor elements Z1, Z2 are connected. For each transmission electrode SE of the two sensor elements Z1, Z2 a connection to the sensor electronic unit S is provided. The compensation electrode KE is connected by means of a common electric main to a particular connection of the sensor electronic unit S. Also the reception electrodes EE of the two sensor elements are connected by means of a common electric main to a particular connection of the sensor electronic unit S.

According to the embodiment shown in FIG. 4, the two sensor elements Z1, Z2 may be operated for example in a time-division multiplexing, i.e. the transmission electrodes SE of the sensor elements are each supplied with an electric alternating voltage sequentially. Therefore also an alternating electrical field is emitted sequentially at both transmission electrodes SE, which is coupled into the respective reception electrode EE, so that a current flows in the respective reception electrode. By supplying the transmission electrodes SE sequentially with an electric alternating voltage, the current detected by the evaluating device A may be precisely assigned to a reception electrode EE and thus also to a sensor element.

Figure 5:
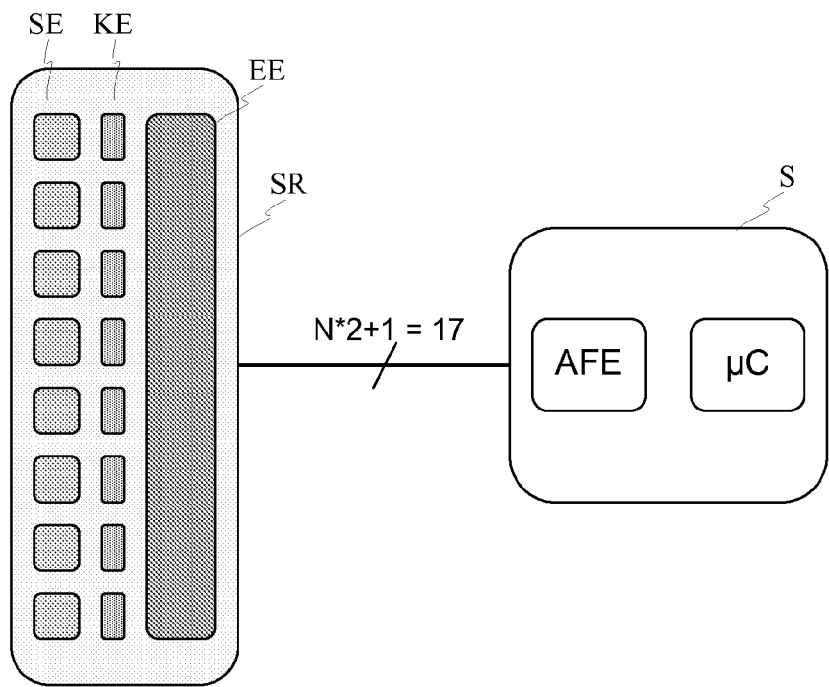
FIG. 5 an application example of a sensor electronics according to the invention with a plurality of sensor elements as a capacitive slide control.

FIG. 5 shows an application of a capacitive sensor device with a sensor electronic unit S and a plurality of sensor elements.

The application shown in FIG. 5 is a capacitive slide control SR, which comprises eight sensor elements, wherein the eight sensor elements use a common reception electrode EE. The coupling of the sensor elements to the sensor electronic unit S substantially corresponds to the coupling shown in FIG. 3.

The sensor electronic unit S may implement in this respect the multiplexing described in regard to FIG. 3, in order to detect or establish the position of a finger at the slide control SR.

As already described in regard to FIG. 2, a first alternating electrical field is emitted at each transmission electrode SE and coupled into the reception electrode EE. Also a second alternating electrical field is emitted at each compensation electrode KE and coupled into the reception electrode EE. The coupled electric alternating fields at the reception electrode EE generate in it an electric current, which may be detected and analysed by the sensor electronic unit S.

For the connection of the capacitive slide control SR or the sensor elements of the slide controls on the sensor electronic unit, seventeen connectors must be provided for the eight sensor elements shown here at the sensor electronic unit S, only one connection being needed for the connection of the reception electrode EE. The sensor electronic unit disposes here of an analogous Front-end (AFE), which evaluates the signal applied at the reception electrode EE and/or the electric current flowing into the reception electrode EE and converts one or more digital signals and supplies a microcontroller μC. The microcontroller may process digital signals and on the basis of a result may induce an action in an electric device which is coupled with the capacitive slide control.

If a finger moves along the slide control SR, the finger influences the respective electric alternating field, which causes a change of the electric current at the reception electrode EE. This change of the electric current is evaluated by the sensor electronic unit S, in which by the evaluation, as already described in regard to FIG. 3, a position of the finger relative to the slide control SR can be determined. In this respect it is not necessary that the finger touches the sensor elements. It is sufficient that the finger is in movement along the capacitive slide control in the observation areas of the sensor elements. As the sensor elements may be arranged very close to each other by an appropriate choice of the multiplexing method, a very compact capacitive slide control SR may be provided, which nevertheless comprises a high resolution, i.e. the position of the finger relative to the slide control SR may be particularly clearly defined. This is possible because an interaction of the multiplexing sensor elements is avoided by an appropriate selection or is recognized by the sensor electronic unit S accordingly.

It is also possible to detect the position of several fingers on the slide control. For this purpose it is provided to lead the sensor signal at the entry at which the reception electrode is connected, to a signal analysis. The signal analysis, for example in case of application of the frequency multiplexing, may break up the sensor signal into the frequency components with an amplitude. From the amplitudes of the frequency components may be deduced if only one finger (amplitudes only present one peak value) or several fingers (amplitudes present several peak values) are placed on the capacitive slide control.

Alternatively the slide control shown in FIG. 5 may also be implemented with a transmission electrode, a compensation electrode and a plurality of reception electrodes.

Figure 6:
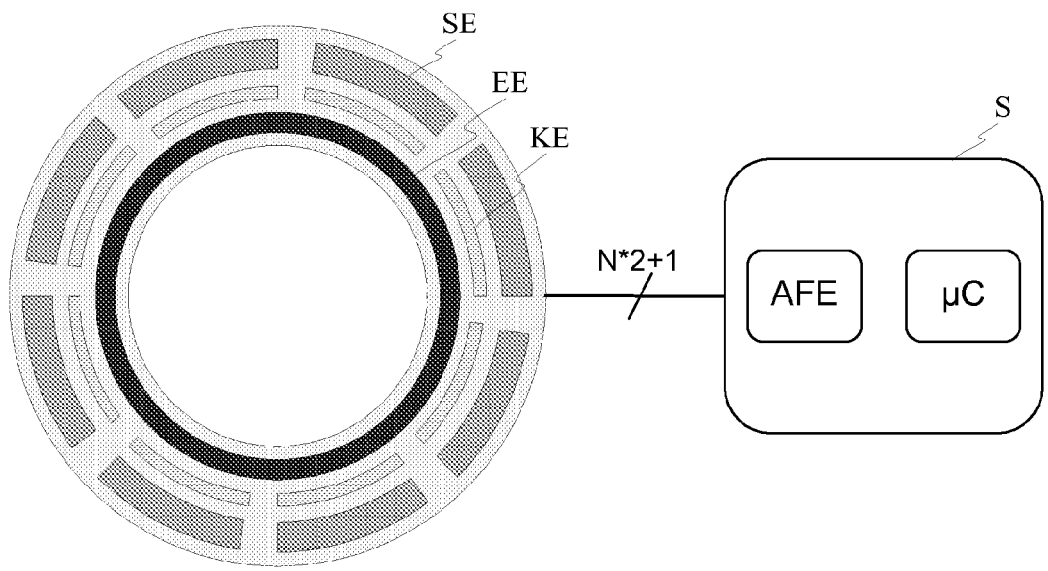
FIG. 6 another application example in the form of a capacitive rotary regulator.

In FIG. 6 another application of a capacitive sensor is shown, with a sensor electronic unit S and a plurality of sensor elements connected to it. In this case it is a capacitive rotary regulator. The connection of the sensor elements here again corresponds to the embodiment shown in FIG. 3, i.e. the sensor elements have a common reception electrode EE. The sensor electronic unit S here again has seventeen connectors for the connection of the sensor elements to the sensor electronic unit S, because the capacitive rotary regulator is provided with eight sensor elements.

Alternatively the rotary control shown in FIG. 6 may also be implemented with a transmission electrode, a compensation electrode and a number of reception electrodes. In order to reach an even better resolution of a finger's position relative to a plurality of sensor elements, it is advantageous to use an interpolation method, which is provided by this invention.

Figure 7:
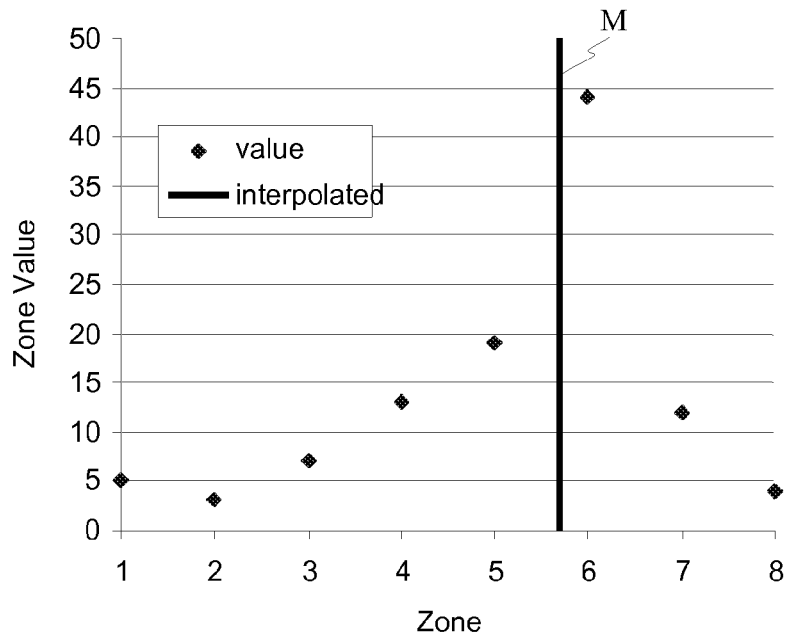
FIG. 7 an example for the interpolation of a position of an object relative to a plurality of sensor elements.

In FIG. 7 the result of a linear interpolation method is shown, which shows, for eight sensor elements, an interpolation of the position of a finger relative to the eight sensor elements. Along the X axis the eight sensor elements are applied, on the basis of an ordinal number. Preferably an adjacent relationship of the sensor elements is defined by ordinal numbers, i.e. for example the sensor element with the ordinal number 4 has as direct neighbour the sensor element with the ordinal number 3 or with the ordinal number 5.

On the Y axis the discrete signal values detected for the respective sensor elements are applied. The signal values may correspond for example to a current in the reception electrode EE of the respective sensor elements.

The marking M shown in FIG. 7 corresponds here to the interpolated position of an object relative to the eight sensor elements. These eight sensor elements may be those eight sensor elements shown in regard to FIG. 5 or in regard to FIG. 6. As it may be recognized from FIG. 7, the resolution of a position determination can be clearly increased, so that in addition to the possibility already described with FIG. 5, of being able to arrange the sensor elements particularly close to each other, the resolution may be even further reinforced and a still more precise capacitive slide controller may be provided.

Instead of the linear interpolation method shown here it may be also provided a higher grade interpolation method, e.g. a square or a spline interpolation.

Figure 8:
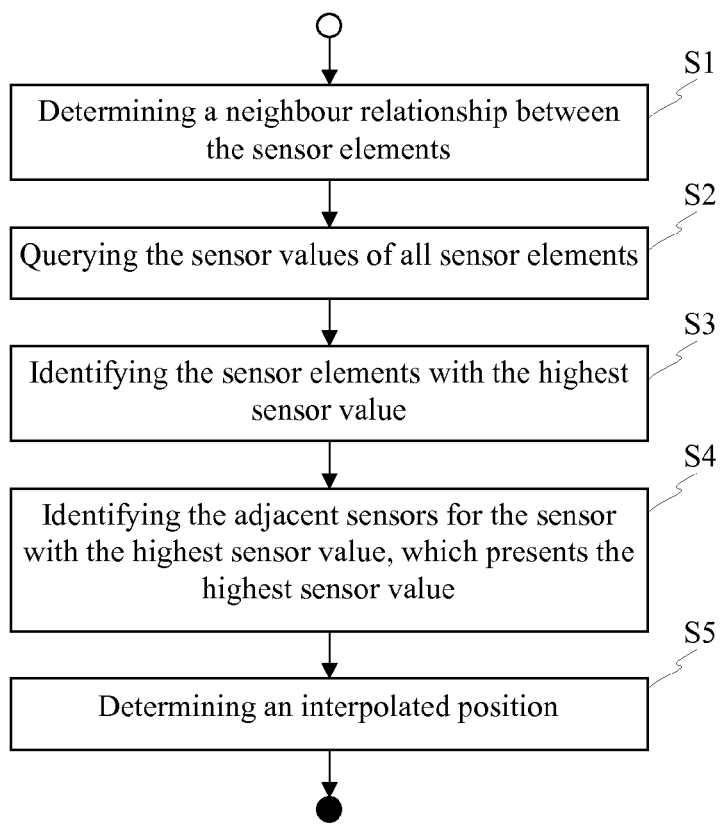
FIG. 8 a flowchart of a method for determining an interpolated position of an object relative to a number of sensor elements.

In FIG. 8 is shown an example of a linear interpolation method according to the invention in the form of a flowchart. In a first step S1, the neighbour relationships between the single sensor elements are determined, i.e. to each sensor element an ordinal number is assigned. For example this first step S1 can be executed once during an initialisation process of a capacitive sensor or of the sensor electronic unit S. The ordinal numbers may be also stored in a non-volatile memory in the sensor electronic unit.

When the sensor is working, the sensor values of all sensor elements are queried, S2. A sensor value can indicate the presence of an object in the observation area of the respective sensor element. The presence of an object in an observation area may be for example the distance of an object to a sensor element.

The queried sensor values may be stored in the evaluating device for further processing in a storage device or in several registers.

In a further step S3 the sensor element is determined which shows the highest sensor value, for example the highest current. For this detected sensor element, the ordinal number and the sensor value are buffered.

In the next step S4 that adjacent sensor is determined which shows the highest sensor value. In the example in FIG. 7, the sensor element with the ordinal number 6 is that sensor element which shows the greatest sensor value, i.e. 45. The adjacent sensor elements to the sensor element with the ordinal number 6 are therefore the sensor elements with the ordinal numbers 5 and 7. Out of the sensor elements with the ordinal number 5 and 7 that sensor element is selected which shows the greatest sensor value, i.e. the sensor element with the ordinal number 5 is selected. The ordinal number and the sensor value for the detected adjacent sensor element are also buffered in a storage device.

In the next step S5, an interpolated position is now determined or calculated. In one embodiment of the invention, the interpolated position may be calculated on the basis of the following formula:

$$\frac{n_1 \cdot v_1 + n_2 \cdot v_2}{v_1 + v_2}$$

in which $n_1$ is the ordinal number of the first sensor element, $n_2$ is the ordinal number of the second sensor element, $v_1$ is the value of the detected electric variable of the first sensor element and $v_2$ is the value of the detected electric variable of the second sensor element. That results in an interpolated position M of an object relative to the sensor elements, in which in this case the position lies between M two discrete positions of the sensor elements with the ordinal number 5 or 6.

According to the invention, still further adjacent sensor elements may be involved in the interpolation, so that a generalized interpolation formula results:

$$\frac{\sum n_1 \cdot v_1}{\sum v_1}$$

in which $n_1$ is the ordinal number of the i-th sensor element and $v_1$ is the value of the detected electric variable of the i-th sensor element. In this way it is possible to even further increase the precision of an object position relative to the sensor elements.

Figure 9:
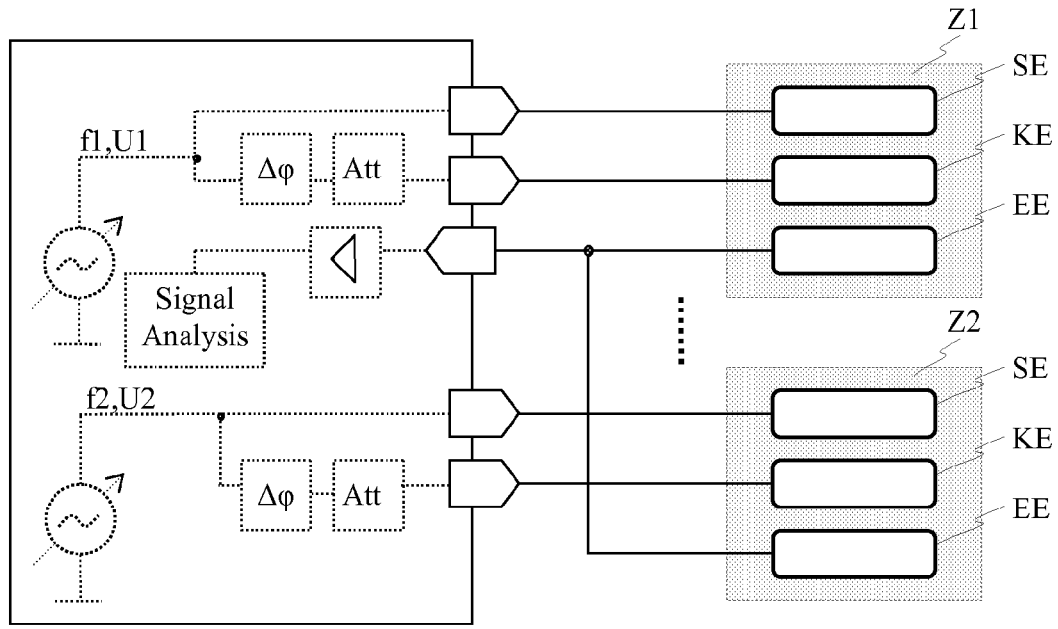
FIG. 9 another embodiment of a sensor electronics according to the invention, whereby the sensor elements are operated in the frequency multiplexing method.

FIG. 9 shows an embodiment of the sensor electronic unit according to the invention to which two sensor elements Z1 and Z2 are connected. The connection of the sensor elements Z1, Z2 to the sensor electronic unit S corresponds to the connection of the sensor elements to the sensor electronic unit 5, as shown in regard to FIG. 3. In the embodiment shown in FIG. 9, the sensor elements Z1, Z2 are exclusively operated in the frequency multiplexing method. In this respect each transmission electrode SE is supplied with an electric alternating signal, which comprises each time a different frequency $f_1$ or $f_2$. The amplitudes $U_1$, $U_2$ of the electric alternating signals may be identical, however they may also be different. The compensation electrodes KE of the two sensor elements are also supplied with an electric alternating signal, the frequency of the respective signal corresponding to the frequency of the alternating signal which is supplied at the respective transmission electrode SE of the sensor element. The electric alternating signal at the compensation electrode KE is dephased with respect to the electric alternating signal at the respective transmission electrode SE.

The reception electrodes EE of the two sensor elements Z1, Z2 are coupled by means of a common electric main with an entry of the sensor electronic unit S. The sensor signal applied to the reception electrodes EE, i.e. the current flowing through the reception electrodes EE, is conducted to a signal analysis, in order to separate the different frequencies in the total current. The separated frequencies may be then assigned again precisely to a reception electrode EE or a sensor element Z1, Z2. Alternatively the sensor signal applied to the reception electrodes EE may be amplified before it is conducted to the signal analysis.

Figure 10:
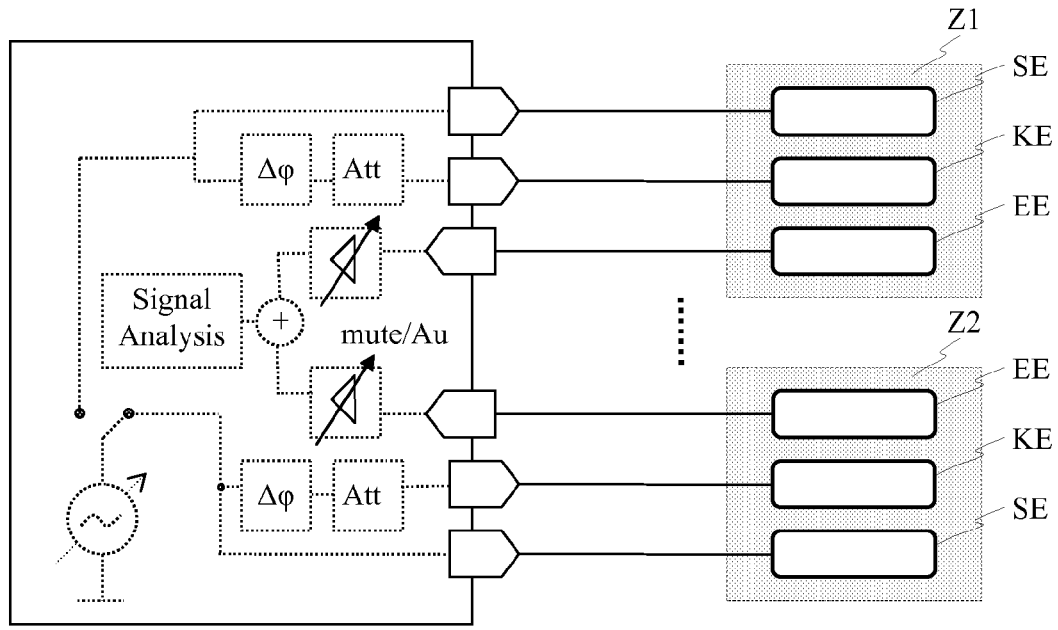
FIG. 10 a further embodiment of a sensor electronics according to the invention, whereby the transmission and the compensation electrodes of the sensor elements are operated by time division method and the currents of the reception electrodes are added and if necessary faded out.

FIG. 10 shows a further embodiment of a sensor electronic unit S according to the invention. The connection of the sensor elements Z1, Z2 to the sensor electronic unit S corresponds to the connection of the sensor elements in FIG. 1, The transmission electrodes SE and the compensation electrodes EE are supplied with an electric alternating signal by time division, i.e. the sensor elements Z1, Z2 are supplied with an electric alternating signal sequentially. Here, too, the electric alternating signal applied at the compensation electrode ICE is dephased with respect to the electric alternating signal, with which the respective transmission electrode SE is supplied.

The reception electrodes EE of the two sensor elements are each coupled with an evaluating device by means of an entry of the sensor electronic unit S. The evaluating device may include a signal analysis. The sensor signals at both entries, i.e. the currents flowing through both reception electrodes EE will be added and conducted to a signal analysis. The adding of the input signals has the advantage that a detection of an object in an observation area of the sensor elements can take place much faster, because there is no need to recalibrate the operation area of the evaluation path every time.

The sensor signals applied at the entries of the sensor electronic unit S, i.e. electrode currents, may be conducted to an amplifier before being conducted to the adder. The amplifiers are provided in order to fade out the electrode current of those reception electrodes EE which at the moment are not active because of the sensor elements activated by time division. As shown in FIG. 10, the sensor element Z2 is active, i.e. the transmission electrode and the compensation electrode of the sensor element Z2 are each supplied with an electric alternating signal. The alternating electric field emitted at the transmission electrode or at the compensation electrode is coupled in the reception electrode EE of the second sensor element Z2, so that an electric current flows through the reception electrode EE, which is detected by the evaluation unit of the sensor electronic unit S.

As the first sensor element Z1 is not active, the current flowing through the reception electrode EE of the first sensor element can also be faded out, which may be done by the adjustable amplifier. The amplifier is formed in such way that the current in the activated state of the corresponding sensor element is substantially reduced to zero. Instead of the adjustable amplifier also a single-stage amplifier may be provided.

By fading out the electrode currents of the respective not-active sensor elements, the influences of these electrode currents on the total current are avoided or reduced.

Figure 11:
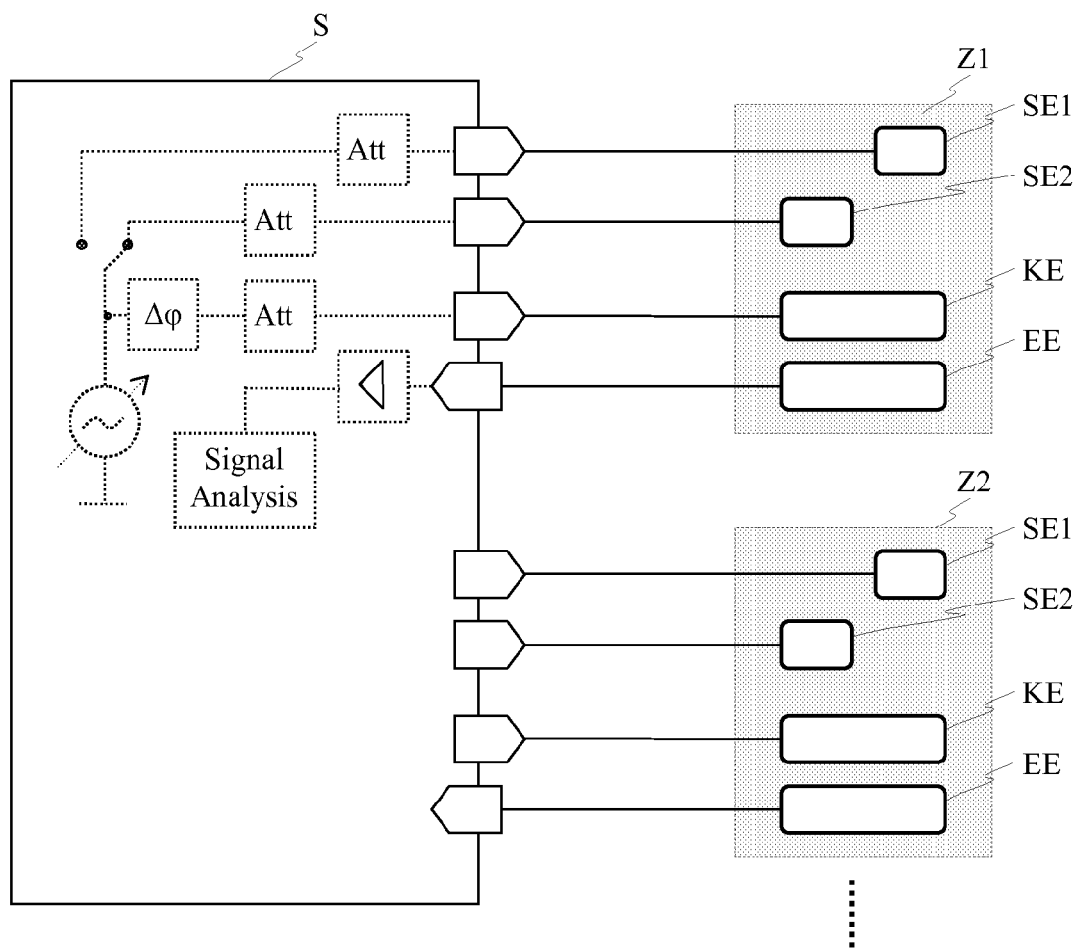
FIG. 11 a further embodiment of a sensor electronics according to the invention, whereby the sensor elements have each several transmission electrodes, which may be operated by time division method.

FIG. 11 shows another embodiment of a sensor electronic unit according to the invention. In this embodiment the sensor elements Z1 and Z2 comprise two correspondent transmission electrodes SE1 and SE2 as well as a corresponding compensation electrode KE and a corresponding reception electrode EE. The sensor elements Z1 and Z2 may be operated according to a multiplexing method, as it has been already described for example in regard to FIG. 1 or FIG. 10.

The electrodes of the single sensor elements can be operated in a multiplexing method as well. In a variant of execution, as shown in FIG. 11, the transmission electrodes SE1 and SE2 may be supplied with an electric alternating signal in the time-division multiplexing, i.e. sequentially. To the compensation electrode KE each time an electrical alternating signal is conducted, the frequency of which corresponds to the electric alternating signal applied at the electrode SE1 or SE2, which however is dephased with respect to this. The reception electrode of the first sensor element Z1 is connected to an entry of the sensor electronic unit S and coupled by means of it with a signal evaluation. Here too, the sensor signal at the entry may be at first conducted to an amplifier. Because of the consecutive supply, i.e. sequentially, of the transmission electrodes SE1 or SE2 with the electric alternating signal, the sensor signal supplied at the entry, i.e. the electrode current flowing through the entry of the reception electrode EE, may be also precisely related with a transmission electrode.

There may be also provided several corresponding compensation electrodes KE and/or several reception electrodes EE for each sensor element. The operation of several compensation electrodes and/or several reception electrodes together with a transmission electrode and/or together with several transmission electrodes may be operated according to one of the described multiplexings in regard to FIG. 1 to FIG. 4, as well as FIG. 9 and FIG. 10.

As precisely shown in FIG. 1 to FIG. 6 as well as in FIG. 9 to FIG. 11, the compensation electrode is each time arranged between the transmission electrode and the reception electrode.

What is claimed is:

1. A system comprising
an electronic circuit with a plurality of connections coupled with a plurality of sensor elements, wherein each sensor element of the plurality of sensor elements comprises a transmitting electrode and a compensation electrode which are associated only with one sensor element, and a reception electrode that can be associated with more than one sensor element, wherein for each sensor element the compensation electrode being capacitively coupleable with the reception electrode, wherein the compensation electrode being arranged between the transmitting electrode and the reception electrode of the sensor element and wherein an alternating electrical field emitted at the sensor element forms an observation area of the sensor element;
and
wherein the electronic circuit being configured to generate for each sensor element first and second transmission signals fed to the transmitting electrode and the compensation electrode of each sensor elements, respectively to form an electric alternating field at the sensor elements by a first alternating electric field emitted at the transmitting electrode and by a second alternating electric field emitted at the compensation electrode each received at the reception electrode and to detect the presence of an object in at least one observation area of the sensor elements, wherein the sensor elements are distinguished from each other by multiplexing.

2. The electronic circuit according to claim 1, wherein the first alternating electric field and the second alternating electric field being coupleable into the reception electrode and the second transmission signal is derived from the first transmission signal.

3. The electronic circuit according to claim 2, wherein the first alternating electric field emitted at the transmission electrode being coupleable into the reception electrode when an object enters the observation area of the sensor element.

4. The electronic circuit according to claim 1, wherein each transmitting electrode and each compensation electrode of each sensor element is connected through an associated connection with the electronic circuit and the reception electrodes of all sensor elements are connected via a single connection with the electronic circuit, the electronic circuit being configured
to supply a first alternating voltage to a transmitting electrode of a selected sensor element,
to supply a second alternating voltage to a compensation electrode of the selected sensor element, and
to detect a current from a reception electrode of the selected sensor element,
wherein for each sensor element the first alternating voltage and the second alternating voltage have the same frequency and are dephased with each other.

5. The electronic circuit according to claim 1, wherein multiplexing is accomplished by frequency multiplexing and wherein each sensor element is driven a different frequency.

6. The electronic circuit according to claim 5, wherein a single connection of the electronic circuit is connected with the reception electrodes of the sensor elements and wherein the electronic circuit submits the total current, which results from the current flowing in the respective reception electrodes, to a frequency analysis in order to determine a value for every reception electrode, which is representative for the presence of the object at the corresponding sensor element.

7. The electronic circuit according to claim 1, wherein the multiplexing is accomplished by time division multiplexing and wherein the electronic circuit being configured to supply the transmission electrodes of the sensor elements sequentially with the first alternating voltage.

8. The electronic circuit according to claim 1, wherein multiplexing is accomplished by time division multiplexing and wherein the electronic circuit being configured to detect sequentially the current flowing through the respective reception electrodes of the sensor elements and to determine a value from the detected current which is representative for the presence of the object at the respective sensor element.

9. The electronic circuit according to claim 1, wherein multiplexing is accomplished by code division multiplexing and wherein the electronic circuit being configured to code the first alternating voltages, with which the transmission electrodes of the sensor elements are supplied, each time with a different code.

10. The electronic circuit according to claim 9, wherein the electronic circuit being configured to submit the total current, which results from the current flowing through the respective reception electrodes, to a decoding process, in order to determine a value for each reception electrode which is representative for the presence of the object at the respective sensor element.

11. The electronic circuit according to claim 1, wherein each transmission electrode of each sensor element is connected through an associated connection with the electronic circuit and the compensation electrodes and receiving electrodes of all sensor elements are connected via a single connection, respectively with the electronic circuit.

12. The electronic circuit according to claim 1, wherein the reception electrodes of the sensor elements being formed by means of a common reception electrode, wherein a connection of the electronic circuit is provided for connecting the common reception electrode.

13. The electronic circuit according to claim 1, wherein each reception electrode of each sensor element is connected through an associated connection with the electronic circuit and the transmitting electrodes and compensation electrodes of all sensor elements are connected via a single connection, respectively with the electronic circuit.

14. The electronic circuit according to claim 1, wherein each sensor element comprises an associated reception electrode.

15. A method for determining the position of at least one object by a plurality of sensor elements,
wherein each sensor element of the plurality of sensor elements corn electrode and a compensation electrode which are associated only with one sensor element, and a reception electrode that can be associated with more than one sensor element, wherein for each sensor element the compensation electrode being capacitively coupleable with the reception electrode, wherein the compensation electrode being arranged between the transmitting electrode the reception electrode of the sensor element and wherein an alternating electrical field emitted at the sensor element forms an observation area of the sensor element;
the method comprising:
generating an electric alternating field at least one sensor element by a first alternating electric field emitted at the transmitting electrode by means of a first transmission signal and by a second alternating electric field emitted at the compensation electrode by means of a second transmission signal which is may be derived from the first transmission signal, wherein the first alternating electric field and the second alternating electric field are coupled into the reception electrode, and by using a multiplexing method for all sensor elements, wherein an electric variable is detected for each sensor element which is indicative for the presence of the object in the respective observation area.

16. The method according to claim 15, wherein the second transmission signal is derived from the first transmission signal.

17. The method according to claim 16, wherein the first alternating electric field and the second alternating electric field are coupled into the reception electrode.

18. The method according to claim 17, wherein the first alternating electric field emitted at the transmission electrode is coupled into the reception electrode when an object enters the observation area of the sensor element.

19. The method according to o claim 15, wherein an interpolation is carried out between the detected electric variables, in order to determine an interpolated position of the at least one object relative to the sensor elements.

20. A system comprising
an electronic circuit with a plurality of connections coupled with a plurality of sensor elements, wherein each sensor element of the plurality of sensor elements comprises a transmitting electrode which is associated only with one sensor element, and a compensation electrode and a reception electrode that can be associated with more than one sensor element, wherein for each sensor element the compensation electrode being capacitively coupleable with the reception electrode, wherein the compensation electrode being arranged between the transmitting electrode and the reception electrode of the sensor element and wherein an alternating electrical field emitted at the sensor element forms an observation area of the sensor element; and
wherein the electronic circuit being configured to generate for each sensor element first and second transmission signals fed to the transmitting electrode and the compensation electrode of each sensor elements, respectively to form the electric alternating field at the respective sensor element by a first alternating electric field emitted at the transmitting electrode and by a second alternating electric field emitted at the compensation electrode each received at the reception electrode and to detect the presence of an object in at least one observation area of the sensor elements, wherein the sensor elements are distinguished from each other by multiplexing.

* * * * *

UNITED STATES PATENT AND TRADEMARK OFFICE
CERTIFICATE OF CORRECTION

PATENT NO. : 8,933,705 B2  
APPLICATION NO. : 13/508776  
DATED : January 13, 2015  
INVENTOR(S) : Kaltner et al.

Page 1 of 1

It is certified that error appears in the above-identified patent and that said Letters Patent is hereby corrected as shown below:

In the Claims

Column 13,  
Claim 5, line 56, "...multiplexing is accomplished by frequency multiplexing and wherein..."  
---Change to--- "...multiplexing is accomplished by frequency multiplexing wherein..."

Column 13,  
Claim 7, line 66, "...The electronic circuit according to claim 1, wherein the multiplexing..."---Change to--- "... The electronic circuit according to claim 1, wherein multiplexing..."

Column 14,  
Claim 15, line 47, "...elements corn electrode and a compensation electrode..." ---Change to--- "... elements comprises a transmitting electrode and a compensation electrode..."

Signed and Sealed this  
Twenty-eighth Day of April, 2015

Michelle K. Lee  
*Director of the United States Patent and Trademark Office*